(12) United States Patent
Masaki

(10) Patent No.: US 8,979,341 B2
(45) Date of Patent: Mar. 17, 2015

(54) LIGHT SOURCE APPARATUS AND LIGHT-ADJUSTING METHOD FOR LIGHT SOURCE APPARATUS

(71) Applicant: Olympus Medical Systems Corp., Tokyo (JP)

(72) Inventor: Takahiro Masaki, Kawasaki (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 14/155,442

(22) Filed: Jan. 15, 2014

(65) Prior Publication Data

US 2014/0192551 A1    Jul. 10, 2014

Related U.S. Application Data

(63) Continuation of application No. PCT/JP2013/065549, filed on Jun. 5, 2013.

(30) Foreign Application Priority Data

Sep. 18, 2012  (JP) ................. 2012-204718

(51) Int. Cl.
*A61B 1/06* (2006.01)
*G02B 23/24* (2006.01)
*A61B 1/00* (2006.01)

(52) U.S. Cl.
CPC .......... *A61B 1/0661* (2013.01); *G02B 23/2469* (2013.01); *A61B 1/00006* (2013.01); *A61B 1/0638* (2013.01); *A61B 1/0646* (2013.01); *A61B 1/0669* (2013.01)
USPC ...................................... 362/574

(58) Field of Classification Search
USPC ........................................ 362/574
See application file for complete search history.

(56) References Cited

U.S. PATENT DOCUMENTS

| 6,635,011 B1 | 10/2003 | Ozawa et al. |
| 2007/0153542 A1* | 7/2007 | Gono et al. ............ 362/574 |
| 2008/0306343 A1 | 12/2008 | Yamazaki |

FOREIGN PATENT DOCUMENTS

| EP | 1 992 275 A1 | 11/2008 |
| JP | 2001-190488 A | 7/2001 |

(Continued)

OTHER PUBLICATIONS

Japanese Office Action dated Feb. 18, 2014 in corresponding Japanese Patent Application No. 2013-557689.

*Primary Examiner* — Anh Mai
*Assistant Examiner* — Hana Featherly
(74) *Attorney, Agent, or Firm* — Scully, Scott, Murphy & Presser, PC

(57) ABSTRACT

A light source apparatus includes: a lamp, a diaphragm device, a CPU that causes the diaphragm device to execute adjustment of an emission amount of illumination light on the basis of a target brightness signal generated based on brightness of an image obtained by picking up an image of a subject; a CPU that switches between illumination modes, and a mode switching switch. During a period after an instruction for switching from one of an illumination mode corresponding to normal light observation mode and an illumination mode corresponding to special light observation mode to the other is given until the switching by the CPU is completed, the CPU causes the diaphragm device to execute adjustment of the emission amount of the illumination light based on a correction value obtained by correcting a current diaphragm value at the time when the instruction for switching is given using a predetermined coefficient.

14 Claims, 7 Drawing Sheets

(56) References Cited

FOREIGN PATENT DOCUMENTS

| | | |
|---|---|---|
| JP | 2005-006856 A | 1/2005 |
| JP | 2005-261974 A | 9/2005 |
| JP | 2007-236416 A | 9/2007 |
| JP | 2009-148487 A | 7/2009 |
| JP | 2011-024726 A | 2/2011 |
| WO | WO 2007/099680 A1 | 9/2007 |

\* cited by examiner

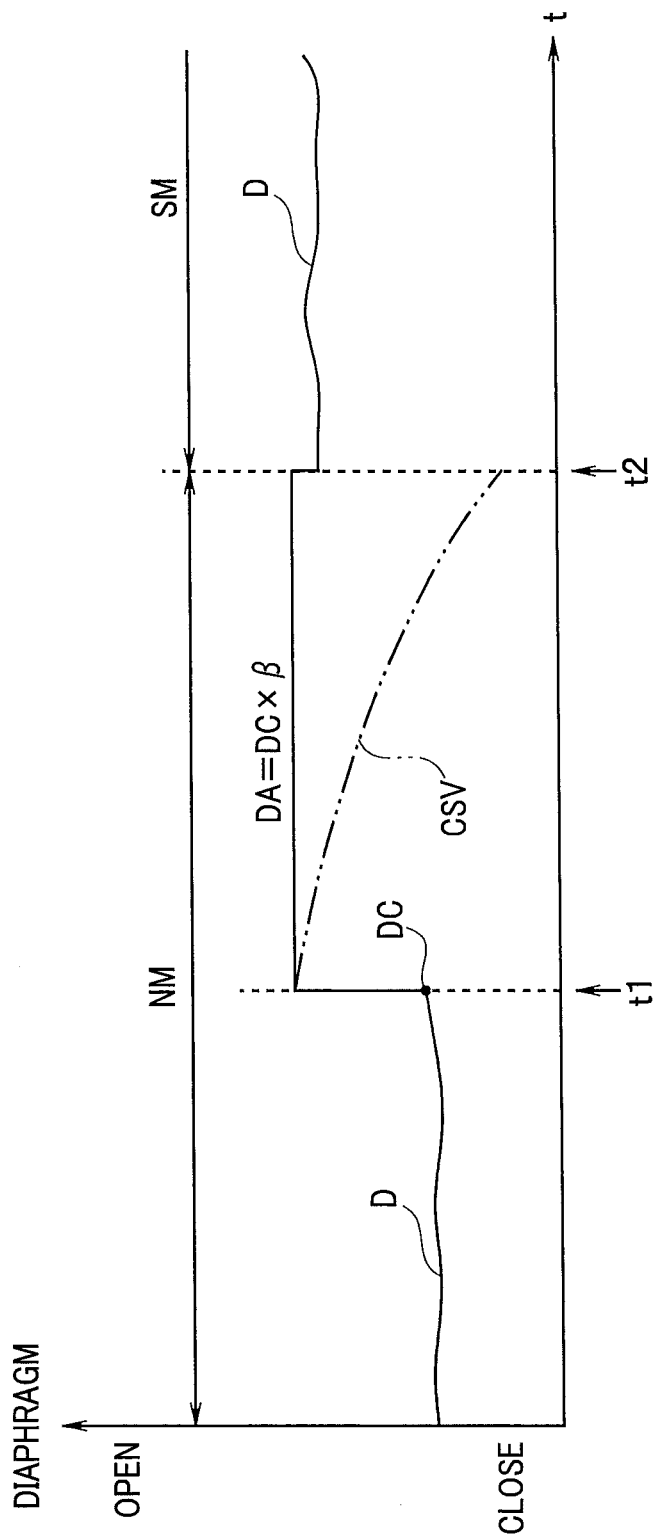

LIGHT SOURCE APPARATUS AND LIGHT-ADJUSTING METHOD FOR LIGHT SOURCE APPARATUS

CROSS REFERENCE TO RELATED APPLICATION

This application is a continuation application of PCT/JP2013/065549 filed on Jun. 5, 2013 and claims benefit of Japanese Application No. 2012-204718 filed in Japan on Sep. 18, 2012, the entire contents of which are incorporated herein by this reference.

BACKGROUND OF THE INVENTION

1. Field of the Invention

The present invention relates to a light source apparatus and a light-adjusting method for the light source apparatus, and more particularly to a light source apparatus including a plurality of illumination modes and a light-adjusting method for the light source apparatus.

2. Description of the Related Art

Conventionally, endoscope apparatuses have been widely used in medical fields and industrial fields. An endoscope apparatus is configured by including an endoscope, a video processor which is a main body apparatus to which the endoscope is connected, a light source apparatus which supplies illumination light to the endoscope, and a monitor on which an endoscopic image subjected to image processing in the video processor is displayed. The endoscopic image inside a subject, which is picked up with the endoscope is displayed on the monitor, and an operator is capable of performing examination and treatment inside of the subject.

In an endoscope apparatus, automatic light adjustment is performed so that an endoscopic image to be displayed on the monitor is displayed with appropriate brightness. The automatic light adjustment is performed by controlling a diaphragm device and a lamp in the light source apparatus on the basis of luminance information on the endoscopic image obtained by performing image processing on an image pickup signal outputted from the image pickup device in the endoscope.

Information related to the brightness of the endoscopic image obtained by picking up an image is supplied from the video processor to the light source apparatus for automatic light-adjustment. The light source apparatus adjusts an amount of the illumination light to be emitted toward the subject on the basis of the information such that the endoscopic image is displayed with appropriate brightness by stopping down a diaphragm of the diaphragm device when the endoscopic image is bright, and by opening up the diaphragm of the diaphragm device when the endoscopic image is dark.

On the other hand, endoscope apparatuses include an endoscope apparatus having a plurality of observation modes. Observation modes include a normal light observation mode in which a subject is irradiated with white light in a visible light band and observed, a special light observation mode in which a subject is irradiated with light in a predetermined band and observed, and other modes. A light source apparatus includes illumination modes corresponding to the observation modes. The endoscope apparatus having a plurality of observation modes enables not only an observation of a subject under normal light but also an observation of the subject under special light by switching the observation modes.

In addition, as disclosed in Japanese Patent Application Laid-Open Publication No. 2009-148487, a light source apparatus is proposed in which a control signal for light amount control is fixed to a predetermined value during switching of the observation modes, in order to improve a response degradation of the light amount control caused by a variation of the illumination light amount which occurs at the time of switching the observation modes.

SUMMARY OF THE INVENTION

A light source apparatus according to one aspect of the present invention includes: a light source for supplying illumination light to a subject; an illumination light amount adjusting section capable of adjusting an emission amount of the illumination light; an illumination light amount control section that causes the illumination light amount adjusting section to execute adjustment of the emission amount of the illumination light on the basis of a light amount control signal generated based on brightness of an image obtained by picking up an image of the subject; an illumination mode switching control section that switches between a first illumination mode in which first light is emitted as the illumination light and a second illumination mode in which second light is emitted as the illumination light, the second light having a wavelength band, at least a part of the wavelength band being different from a wavelength band of the first light; and a switching instruction section that gives an instruction for switching between the first illumination mode and the second illumination mode, wherein, during a period after an instruction for switching from one of the first illumination mode and the second illumination mode to the other of the first and second illumination modes is given by the switching instruction section until the switching by the illumination mode switching control section is completed, the illumination light amount control section maintains the light amount control signal at a predetermined value corresponding to the illumination mode after the completion of the mode switching, and causes the illumination light amount adjusting section to execute adjustment of the emission amount of the illumination light on the basis of the maintained value.

A light-adjusting method for a light source apparatus according to one aspect of the present invention, includes: executing adjustment of an emission amount of illumination light of the light source apparatus on the basis of a light amount control signal generated based on brightness of a subject by an illumination light amount adjusting section of the light source apparatus; and during a period after an instruction for switching from one of a first illumination mode in which first light is emitted as the illumination light and a second illumination mode in which second light having a wavelength band, at least a part of which is different from a wavelength band of the first light, is emitted as the illumination light to the other of the first and second illumination modes is given until the switching is completed, maintaining the light amount control signal at a predetermined value corresponding to the illumination mode after the completion of the mode switching, and executing adjustment of the emission amount of the illumination light on the basis of the maintained value by the illumination light amount adjusting section.

BRIEF DESCRIPTION OF THE DRAWINGS

FIG. 7 illustrates a change in the diaphragm at the time of changing from the normal light observation mode NM to the special light observation mode SM, according to the embodiment of the present invention.

DETAILED DESCRIPTION OF THE PREFERRED EMBODIMENT(S)

Hereinafter, an embodiment of the present invention will be described with reference to the drawings.
(Apparatus Configuration)

Figure 1:
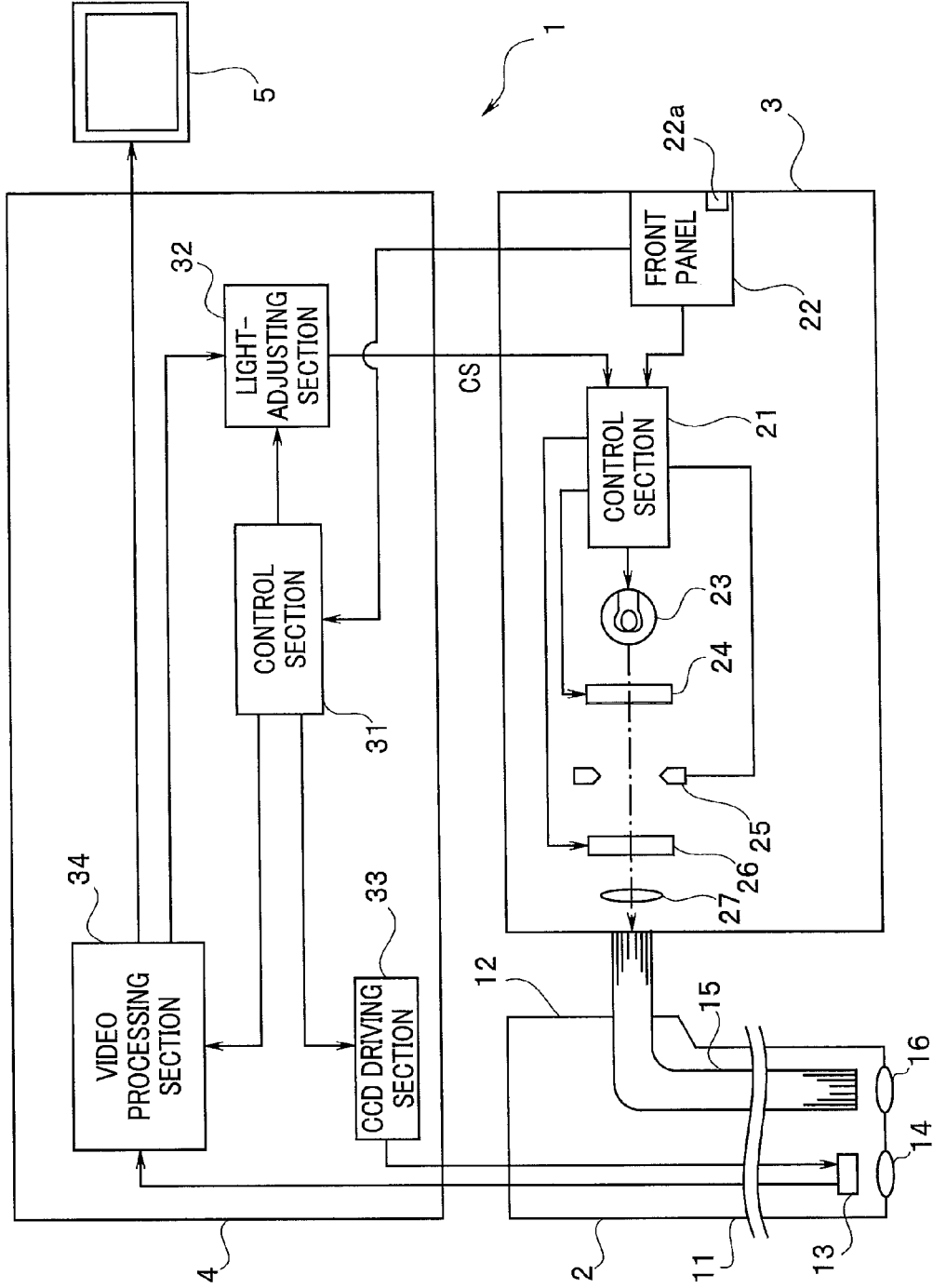
FIG. 1 is a configuration diagram showing a configuration of an endoscope apparatus according to an embodiment of the present invention.

FIG. 1 is a configuration diagram showing a configuration of an endoscope apparatus according to the present embodiment. An endoscope apparatus 1 is configured by including an endoscope 2, a light source apparatus 3, a video processor 4, and a monitor 5. The endoscope 2 and the video processor 4 are connected to each other with a signal cable, not shown, and the light source apparatus 3 and the video processor 4 are also connected to each other with another signal cable, not shown.

The endoscope 2 includes an elongated insertion portion 11 and an operation portion 12. At a distal end portion of the insertion portion 11, a CCD 13 as an image pickup device, an objective optical system 14, one end of a light guide 15 which is an optical fiber inserted through the insertion portion 11, and an illumination optical system 16 are arranged. The endoscope 2 and the light source apparatus 3 are connected to each other with a connection cable (not shown) through which the light guide 15 is inserted. The illumination light from the light source apparatus 3 is emitted through the light guide 15 and the illumination optical system 16, to illuminate a subject. The image of the reflected light from the subject is formed on an image pickup surface of the CCD 13 through the objective optical system 14.

The light source apparatus 3 includes a control section 21, a front panel 22, a lamp 23 as a light source, a first rotary filter 24, a diaphragm device (hereinafter referred to as diaphragm) 25, a second rotary filter 26, and a condensing lens 27.

The control section 21 controls the entirety of the light source apparatus 3, and also controls the lamp 22 and the diaphragm 25 on the basis of a signal related to brightness from the video processor 4. The control section 21 includes a central processing unit (CPU), ROM, RAM, and the like. The configuration of the control section 21 will be described in detail later.

The front panel 22 is provided with a mode switching switch 22a for switching between a normal light observation mode and a special light observation mode, and other various types of operation switches. An operation signal from the front panel 22 is inputted to the control section 21.

The mode switching switch 22a constitutes a switching instruction section that gives an instruction for switching between an illumination mode corresponding to the normal light observation mode and an illumination mode corresponding to the special light observation mode.

In this embodiment, the light source apparatus 3 includes a first illumination mode corresponding to the normal light observation mode and a second illumination mode corresponding to the special light observation mode. Light in a wavelength band for the normal light observation in the normal light observation mode as the first illumination mode is light in a visible light range, and light in a wavelength band for the special light observation in the special light observation mode as the second illumination mode is light in a narrow wavelength band which is a part of wavelength band in the visible light range. That is, the special light is the light having the wavelength band as a part of the wavelength band of the normal light.

Note that, in this embodiment, the light in the illumination mode corresponding to the special light observation mode is the light having the wavelength band which is a part of the wavelength band of the light in the illumination mode corresponding to the normal light observation mode. However, the light in the illumination mode corresponding to the special light observation mode may be light having a wavelength band completely different from the wavelength band of the light in the illumination mode corresponding to the normal light observation mode. That is, in the light source apparatus 3, one of the illumination modes may be a mode in which light having a wavelength band, a part of which is different from the wavelength band of the light in the other of the illumination modes, is emitted as illumination light, or the one of the illumination modes may be a mode in which light having a wavelength band completely different from the wavelength band of the light in the other of the illumination modes is emitted as illumination light.

The lamp 23 is a light source for supplying illumination light to the subject, and is a xenon lamp, for example. The lamp 23 is turned on and off according to a driving signal from the control section 21.

The rotary filter 24 is a filter for selectively emitting either the light in the wavelength band for the normal light observation or the light in the wavelength band for the special light observation. The rotary filter 24 operates so as to rotate around a rotational axis of the rotary filter 24 and arrange a filter corresponding to a mode specified by the mode switching switch 22a on an optical path of the light emitted from the lamp 23 on the basis of a control signal from the control section 21.

The rotary filter 24 is provided insertably into and removably from the optical path of the light emitted from the lamp 23, and in a state of being inserted into the optical path, serves in the special light observation mode as an optical filter which transmits light in a wavelength band which is a part of wavelength band of the light in the normal light observation mode.

Thus, in the special light observation mode, the light source is constituted of the lamp 23 and the rotary filter 24 serving as the optical filter. That is, in the special light observation mode, the light source apparatus 3 is in the illumination mode in which the optical filter is inserted into the optical path and light transmitted by the optical filter is emitted as the illumination light.

The diaphragm 25 is an illumination light amount adjusting section which is capable of adjusting the emission amount of the illumination light to be supplied to the light guide 15. The diaphragm 25 stops down or open up on the basis of the diaphragm driving signal from the control section 21, thereby adjusting the amount of emitted light from the lamp 23.

The rotary filter 26 is a filter including an R (red) filter, a G (green) filter, and a B (blue) filter for emitting frame-sequential light. The rotary filter 26 operates so as to rotate around the rotational axis of the rotary filter 26 at a predetermined rotation speed and continuously arrange the three filters, i.e., the R, G, and B filters in turns on the optical path of the emitted light from the lamp 23, on the basis of the control signal from the control section 21.

The condensing lens 27 is an optical element for condensing the illumination light passed through the two rotary filters 24 and 26 on a proximal end surface of the light guide 15.

The control section 21 of the light source apparatus 3 selects the rotary filter 24 so as to select the filter corresponding to the instruction from the mode switching switch 22a, and controls the diaphragm 25 on the basis of the signal related to brightness from the video processor 4. In the present embodiment, the signal related to brightness is a target brightness signal CS.

The video processor 4 is configured by including a control section 31, a light-adjusting section 32, a CCD driving section 33, and a video processing section 34.

The control section 31 is a processing section for controlling the entirety of the video processor 4, and controls the light-adjusting section 32, the CCD driving section 33 and the video processing section 34 according to the observation mode specified by a user.

The light-adjusting section 32 generates a target brightness signal CS based on the luminance, that is, brightness of a video signal generated by the video processing section 34 and displayed on the monitor 5, to supply the generated target brightness signal to the control section 21 of the light source apparatus 4. The target brightness signal CS is a signal representing a value calculated and determined based on a result of comparison between the brightness of the video signal displayed on the monitor 5 and brightness as reference, for example.

The CCD driving section 33 is a circuit that outputs a CCD driving signal for driving the CCD 13 based on the CCD driving control signal from the control section 31.

The video processing section 33 receives an image pickup signal from the CCD 13 under the control of the control section 31, performs various kinds of correction processing, emphasis processing, and the like, generates a video signal for displaying an endoscopic image on the monitor 5, and outputs the generated video signal to the monitor 5.

The operation signal from the front panel 22 of the light source apparatus 4 is inputted to the control section 31, and the control section 31 executes processing corresponding to a function of a switch operated on the front panel 22.

Figure 2:
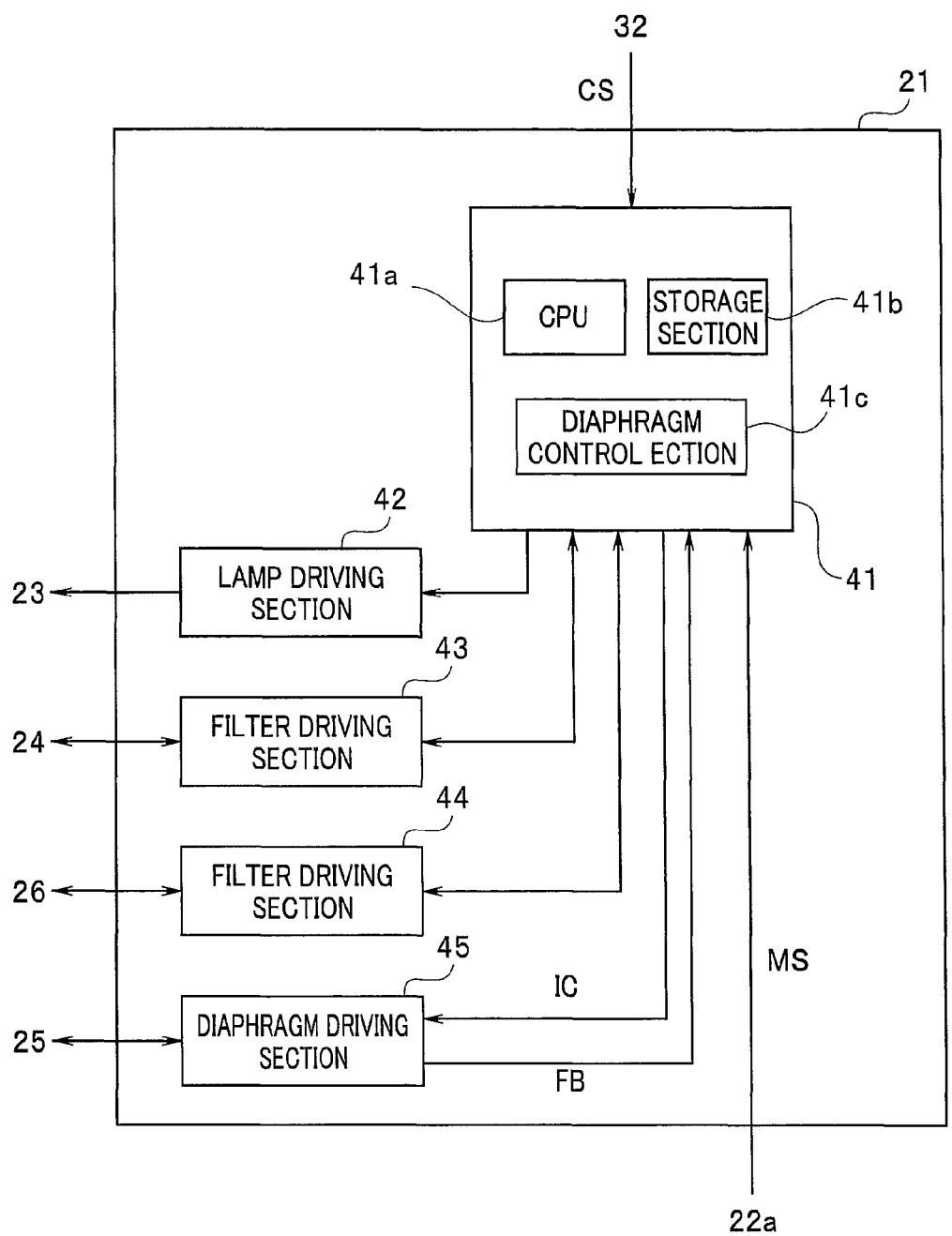
FIG. 2 is a block diagram of a control section 21 of a light source apparatus 3 according to the embodiment of the present invention.

FIG. 2 is a block diagram of the control section 21 of the light source apparatus 3. The control section 21 is configured by various kinds of circuits mounted on a circuit substrate. The control section 21 is constituted of various kinds of chips and circuits mounted on the substrate. The control section 21 includes an FPGA (Field Programmable Gate Array) 41, a lamp driving section 42, filter driving sections 43, 44, and a diaphragm driving section 45.

The FPGA 41 includes a CPU 41a, a storage section 41b including ROM and RAM, and a diaphragm control section 41c. The diaphragm control program to be described later is stored in the storage section 41b, and read by the CPU 41a to be executed.

As described later, the CPU 41a constitutes an illumination mode switching control section that switches between an illumination mode corresponding to the normal light observation mode NM and an illumination mode corresponding to the special light observation mode SM, on the basis of the signal from the mode switching switch 22a.

The diaphragm control section 41c is a control section that outputs a diaphragm driving control signal IC corresponding to the target brightness signal CS from the video processor 4. That is, the diaphragm control section 41c is an illumination light amount control section that causes the diaphragm 25 as the illumination light amount adjusting section to execute adjustment of the emission amount of the illumination light on the basis of the target brightness signal CS which is a light amount control signal generated based on the brightness of the image obtained by picking up the image of the subject.

The target brightness signal CS indicates a target value of brightness, and the diaphragm control section 41c controls the diaphragm 25 such that the target value indicated by the target brightness signal CS (hereinafter target brightness value) CSV becomes a predetermined reference value RS. Specifically, the diaphragm control section 41c generates a diaphragm driving control signal IC for stopping down or opening up the diaphragm 25 depending on whether the inputted target brightness value CSV is larger or smaller than the predetermined reference value RS, to output the generated diaphragm driving control signal to the diaphragm driving section 45. When the inputted target brightness value CSV is equal to the predetermined reference value RS, the luminance (that is, brightness) of the video signal displayed on the monitor 5 is appropriate. Therefore, the diaphragm control section 41c does not output the diaphragm driving control signal IC for stopping down or opening up the diaphragm 25.

Accordingly, the target brightness signal CS is changed by the control of the diaphragm 25 performed by the diaphragm control section 41c. However, when the inputted target brightness value CSV coincides with the predetermined reference value RS, the diaphragm control section 41c does not change the diaphragm value of the diaphragm 25.

The lamp driving section 42 outputs a lamp driving signal for lighting the lamp 23 on the basis of a lamp driving control signal from the FPGA 41.

The filter driving section 43 outputs a motor driving signal for driving a motor (not shown) that causes the rotary filter 24 to rotate, on the basis of a filter driving control signal for controlling the rotary filter 24, which is outputted from the FPGA 41.

The filter driving section 44 outputs a motor driving signal for driving a motor (not shown) that causes the rotary filter 26 to rotate, on the basis of the filter driving control signal for controlling the rotary filter 26, which is outputted from the FPGA 41.

The diaphragm driving section 45 outputs a diaphragm driving signal for driving the diaphragm 25, on the basis of the diaphragm driving control signal IC for controlling the diaphragm 25 from the FPGA 41. A current diaphragm value DC based on a detection signal from a position detector such as a potentiometer provided in the diaphragm 25 is fed back and inputted to the diaphragm driving section 45, and a feed back signal FB of the current diaphragm value is inputted to the diaphragm control section 41c.

Thus, the diaphragm 25 that adjusts the light amount of the illumination light and the diaphragm driving section 45 that drives the diaphragm 25 according to the inputted diaphragm driving control signal IC constitute the illumination light amount adjusting section.

Note that feedback signals indicating the rotational positions of the rotary filters 24, 26 are inputted also to the filter driving sections 43, 44, and also the feedback signals are inputted to the control section 21.

The FPGA 41 receives a mode signal MS indicating a mode specified by the mode switching switch 22a and the target brightness signal CS from the video processor 4.

Figure 3:
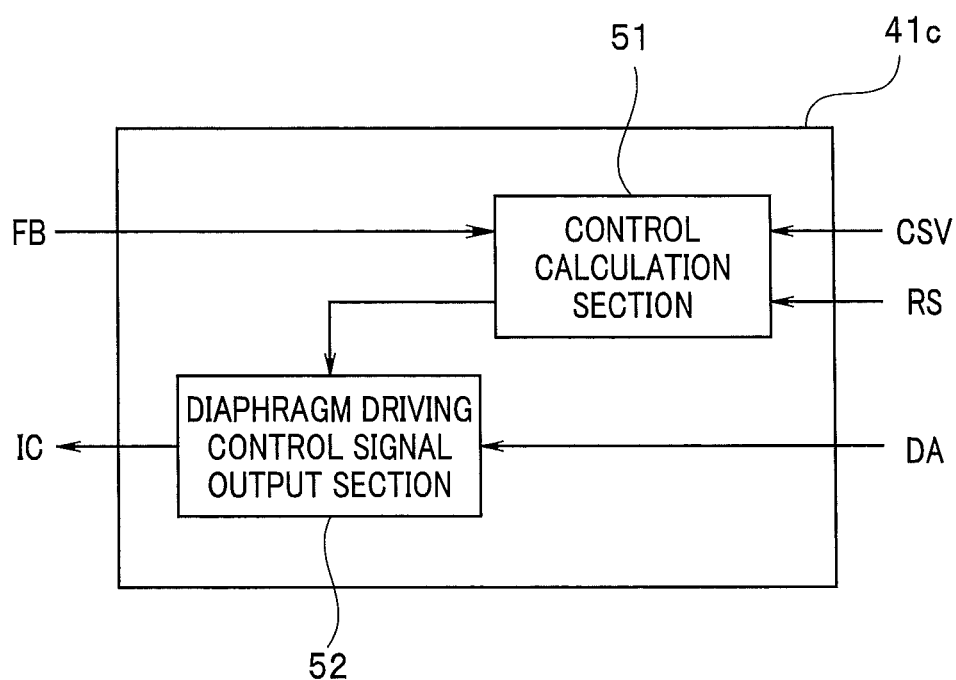
FIG. 3 is a block diagram showing a configuration of a diaphragm control section 41c according to the embodiment of the present invention.

FIG. 3 is a block diagram showing the configuration of the diaphragm control section 41c. The diaphragm control section 41c includes a control calculation section 51 and a diaphragm driving control signal output section 52. The control calculation section 51 receives either the signal of the target brightness value CSV or the signal of the reference value RS, as described later, and on the basis of the inputted signal, the control calculation section generates a control result signal for controlling the diaphragm 25 such that the brightness of the video signal to be displayed on the monitor 5 has appropriate brightness. When the mode is not being switched, the control calculation section 51 receives the target brightness signal CS which is a light amount control signal, to calculate an adjusting value of the emission amount of the illumination light and output the calculated adjusting value as the control result signal.

The diaphragm driving control signal output section 52 generates the diaphragm driving control signal IC corresponding to the control result signal generated by the control calculation section 51 to output the generated diaphragm driving control signal. As described later, under the control by the CPU 41a, during the mode switching, the diaphragm driving control signal output section 52 outputs the diaphragm driving control signal IC corresponding to the correction value DA.

As a whole, in the endoscope apparatus 1, the image pickup signal obtained by the CCD 13 of the endoscope 2 is subjected to image processing in the video processor 4, and the endoscopic image is displayed on the monitor 5. According to the operation of the mode switching switch 22a, the control section 31 controls the video processing section 34 to generate a video signal of the endoscopic image in accordance with the specified observation mode, and causes the generated video signal to be displayed on the monitor 5.

Furthermore, the control section 21 of the light source apparatus 3 controls the diaphragm 25 on the basis of the target brightness signal CS from the video processor 4 and also controls the rotary filter 24 so as to allow a filter corresponding to the operation of the mode switching switch 22a to be selected. When the illumination mode corresponding to the observation mode is switched, control of the diaphragm 25 is performed in the light source apparatus 3 so as to suppress halation or the like.

(Operation)

Figure 4:
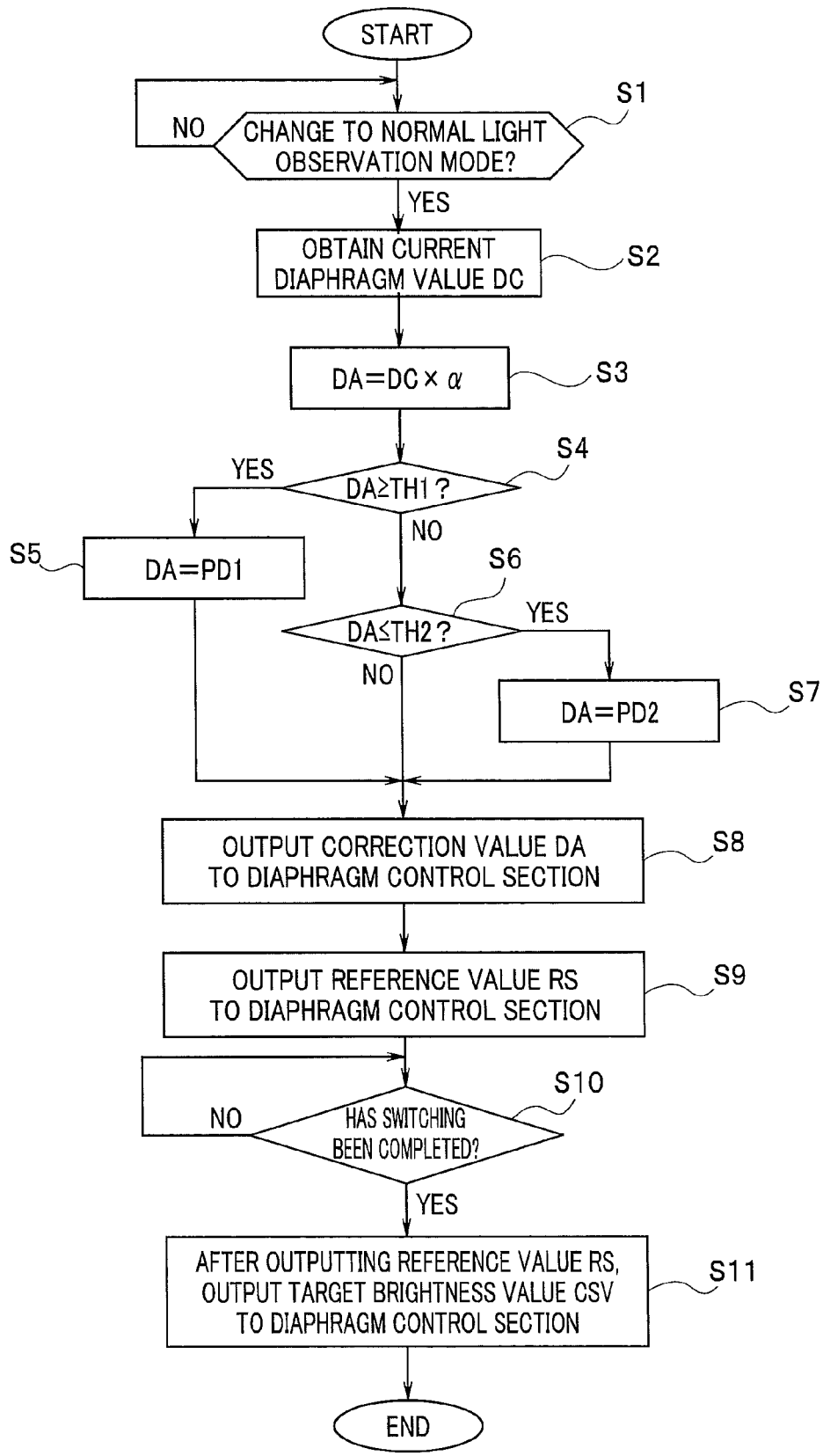
FIG. 4 is a flowchart showing an example of a flow of processing of a diaphragm control program executed by a CPU 41a of an FPGA 41 in a control section 21 at a time of switching from a special light observation mode SM to a normal light observation mode NM, according to the embodiment of the present invention.

FIG. 4 is a flowchart showing an example of a flow of processing of a diaphragm control program executed by the CPU 41a of the FPGA 41 in the control section 21 at the time of switching from the special light observation mode SM to the normal light observation mode NM.

First, when the endoscope apparatus is operated in the special light observation mode SM, the CPU 41a determines whether or not an instruction for changing the observation mode to the normal light observation mode NM is given (S1). When the user as an operator operates the mode switching switch 22a to input the instruction for switching to the normal light observation mode NM into the light source apparatus 4, a mode signal MS indicating the switching signal is inputted to the CPU 41a. As a result, the CPU 41a determines whether or not the instruction for changing the observation mode to the normal light observation mode NM is given.

If the instruction for changing the observation mode to the normal light observation mode NM is not given, no processing is performed. When the instruction for changing the observation mode to the normal light observation mode NM is given (S1: YES), the CPU 41a obtains a diaphragm value as of now (hereinafter, referred to as current diaphragm value) DC on the basis of the feedback signal FB from the diaphragm driving section 45 (S2).

The CPU 41a calculates the correction value DA by multiplying the current diaphragm value DC by a predetermined coefficient $\alpha$ (S3). The predetermined coefficient $\alpha$ is a value larger than 1, and the value is 2, for example.

The predetermined coefficient $\alpha$ may be described in the diaphragm control program, or set in the storage section 41b. In addition, the predetermined coefficient $\alpha$ can be changed according to the type or the like of the endoscope 2, light source apparatus 3 or video processor 4.

Next, the CPU 41a determines whether or not the calculated correction value DA is equal to or larger than a predetermined threshold TH1 (S4). The threshold TH1 is an upper limit value of the correction value DA corresponding to the minimum diaphragm (maximum diaphragm value).

When the correction value DA obtained as a result of multiplication by the predetermined coefficient $\alpha$ is equal to or larger than the predetermined threshold TH1 (S4: YES), the CPU 41a sets the correction value DA to a predetermined fixed value PD1 (S5).

When the correction value DA obtained as a result of multiplication by the predetermined coefficient $\alpha$ is less than the predetermined threshold TH1 (S4: NO), the CPU 41a determines whether or not the calculated correction value DA is equal to or smaller than a predetermined threshold value TH2 (S6). The threshold value TH2 is a lower limit value of the correction value DA corresponding to the maximum diaphragm (minimum diaphragm value).

When the correction value DA obtained as a result of multiplication by the predetermined coefficient $\alpha$ is equal to or smaller than the predetermined threshold value TH2 (S6: YES), the CPU 41a sets the correction value DA to a predetermined fixed value PD2 (S7).

As described above, when the correction value DA exceeds the predetermined upper limit value TH1 or falls below the predetermined lower limit value TH2, the CPU 41a as an illumination mode switching control section changes the correction value DA to the predetermined upper limit value TH1 or the predetermined lower limit value TH2.

After the steps S5, S6 and S7, the CPU 41a outputs the correction value DA to the diaphragm control section 41c (S8), and outputs a reference value RS to the diaphragm control section 41c instead of the target brightness value CSV from the light-adjusting section 32 (S9). Specifically, as shown in FIG. 3, the correction value DA is supplied to the diaphragm driving control signal output section 52, and the reference value RS is supplied to the control calculation section 51.

Then, the CPU 41a determines whether or not the switching from the special light observation mode SM to the normal light observation mode NM is completed (S10). This determination can be performed on the basis of the feedback signal of the rotary filter 24, for example.

If the switching to the normal light observation mode NM is not completed (S10: NO), no processing is performed. When the switching from the special light observation mode SM to the normal light observation mode NM is completed (S10: YES), the CPU 41a outputs the reference value RS to the diaphragm control section 41c, and thereafter outputs the target brightness signal CS to the diaphragm control section (S11). In other words, the CPU 41a controls the input to the control calculation section 51 such that the target brightness signal CS is inputted to the control calculation section 51.

As described above, during a period after the instruction for switching from the illumination mode corresponding to the special light observation mode SM to the illumination mode corresponding to the normal light observation mode NM is given through the mode switching switch 22a until switching by the CPU 41a which is the illumination mode switching control section is completed, the diaphragm control section 41c as the illumination light amount control section causes the diaphragm 25 and the diaphragm driving section 45 to execute adjustment of the emission amount of the illumination light on the basis of the correction value DA obtained by correcting the current diaphragm value DC, which is the light amount control signal at the time when the switching is instructed, using the predetermined coefficient α.

Furthermore, the reason why the reference value RS is outputted to the diaphragm control section 41c first in step S11 is to prevent the target brightness signal CS generated under the observation mode before the switching from being inputted to the diaphragm control section 41c immediately after the switching.

Figure 5:
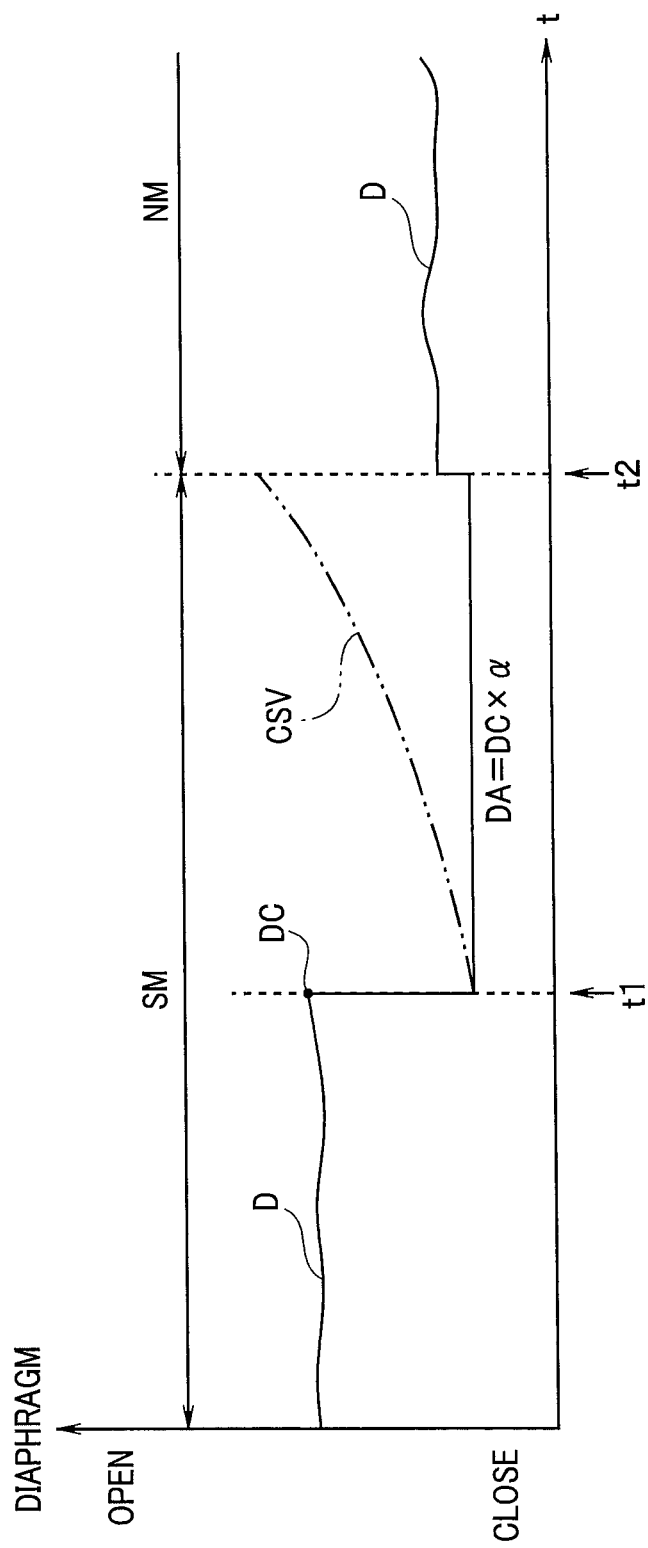
FIG. 5 illustrates a change in the diaphragm at the time of switching from the special light observation mode SM to the normal light observation mode NM, according to the embodiment of the present invention.

FIG. 5 illustrates a change in the diaphragm at the time of switching from the special light observation mode SM to the normal light observation mode NM.

In accordance with the lapse of the time t, a diaphragm value D of the diaphragm 25 changes on the basis of the diaphragm driving control signal IC from the diaphragm control section 41c. The diaphragm control according to the special light observation mode SM is performed until the time t1. Note that the video processor 4 is still in the special light observation mode SM after the time t1 has elapsed.

When the instruction for switching from the special light observation mode SM to the normal light observation mode NM is given at the operation time t1, the processing steps from the above-described steps S2 to S9 are executed.

In the step S3, the CPU 41a calculates the correction value DA obtained by multiplying the current diaphragm value DC at the time when the instruction for switching from the special light observation mode SM to the normal light observation mode NM is given, by the predetermined coefficient α. Then, in the step S8, the CPU 41a controls the diaphragm control section 41c, to control the diaphragm 25 on the basis of the correction value DA. Therefore, from the time t1 to the time t2, the diaphragm driving control signal IC has a constant value, and the diaphragm 25 is maintained at a constant value.

Furthermore, in the step S9, the CPU 41a controls the input to the control calculation section 51 such that, instead of the target brightness value CSV from the light-adjusting section 32, the reference value RS indicating that the diaphragm 25 is appropriately controlled is inputted to the control calculation section 51.

After the time t1, until the rotary filter 24 is rotated to allow the filter for normal light to be appropriately arranged on the optical path of the emitted light from the lamp 23, the light amount of the illumination light with which the subject is irradiated changes. As a result, the luminance of the endoscopic image obtained by the video processing section 34 changes, and the light-adjusting section 32 of the video processor 4 which is in the special light observation mode SM calculates a target brightness signal CS corresponding to the change, to output the calculated target brightness signal CS.

However, since the diaphragm 25 is fixed to the value corresponding to the correction value DA, the target brightness value CSV calculated in the light-adjusting section 32 becomes a value greatly different from the reference value RS after the time t1, as shown in FIG. 5.

After that, at the time t2, when the switching from the special light observation mode SM to the normal light observation mode NM is completed and the endoscope apparatus 1 is brought into the normal light observation mode, the CPU 41a outputs the reference value RS to the diaphragm control section 41c, and thereafter outputs the target brightness signal CS from the light-adjusting section 32 to the control section 41c.

As described above, in the special light observation mode SM, the filter for the special light observation mode SM is selected in the rotary filter 24. The special light is light having the wavelength band which is a part of the wavelength band of the normal light. Therefore, the luminance of the image pickup signal obtained by the CCD 13 is low. Accordingly, the diaphragm 25 is more opened up in the special light observation mode SM than in the normal light observation mode NM. According to the light source apparatus 3 in the above-described embodiment, the diaphragm driving control signal IC corresponding to the correction value DA which is larger than the current diaphragm value DC is outputted until the mode switching is completed, such that the diaphragm value of the diaphragm 25 becomes close to the diaphragm value in the normal light observation mode when the observation mode is switched from the special light observation mode SM to the normal light observation mode NM and the control of the diaphragm 25 is started in the normal light observation mode NM.

After the completion of the mode switching, the diaphragm control section 41 is controlled such that the reference value RS is inputted to the control calculation section 41c of the diaphragm control section 41 and thereafter the target brightness value CSV of the target brightness signal CS from the light-adjusting section 32 is inputted to the control calculation section.

Such control can prevent the entire endoscopic image displayed on the monitor 5 from going white for a moment. Furthermore, since the correction value DA is determined using the current diaphragm value DC at the time of the mode switching, even if the lamp 23 is deteriorated, the entire endoscopic image can be prevented from going white for a moment.

Next, description will be made on control of the diaphragm at the time of switching from the normal light observation mode NM to the special light observation mode SM.

Figure 6:
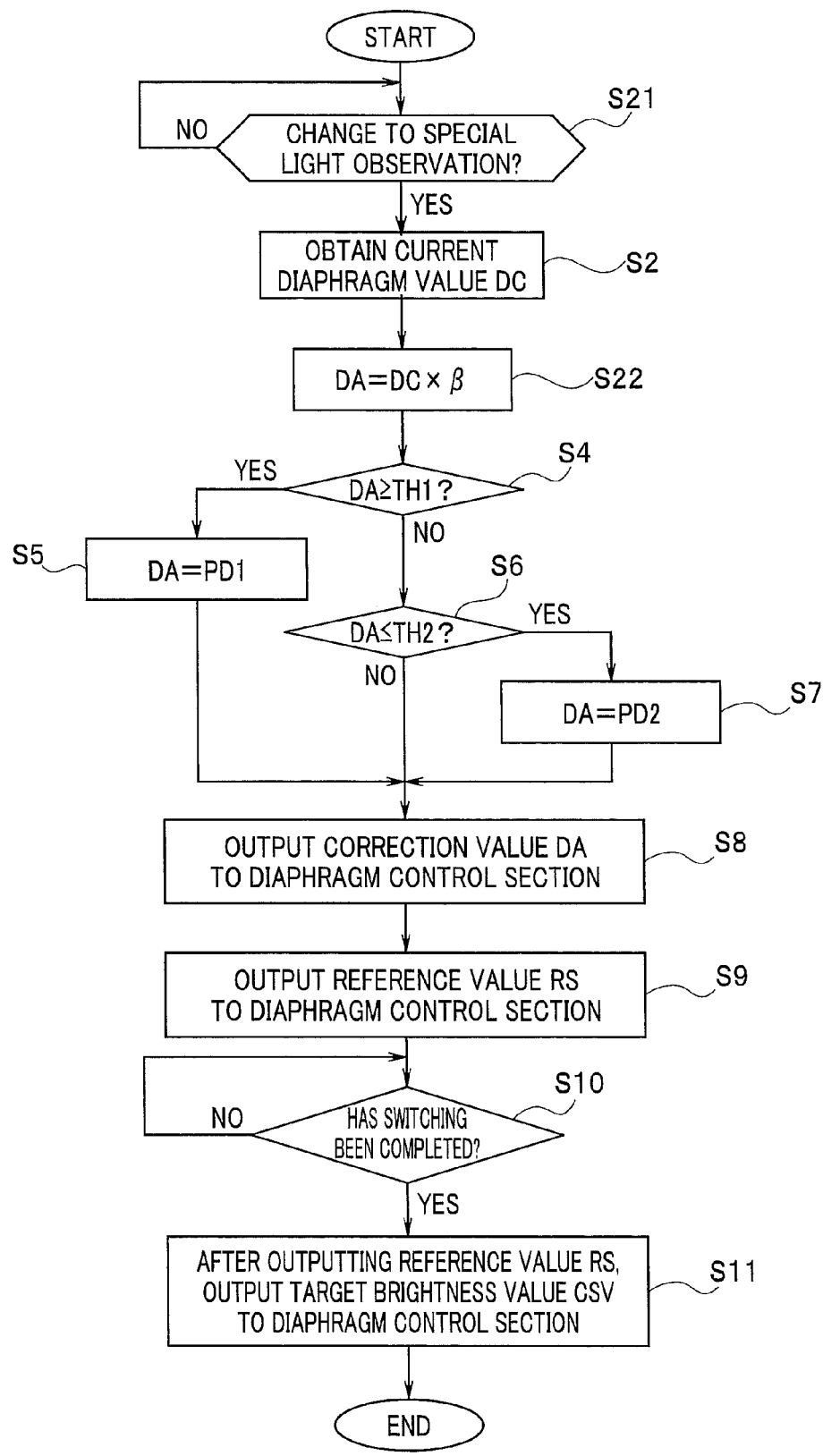
FIG. 6 is a flowchart showing an example of a flow of processing of the diaphragm control program executed by the CPU 41a of the FPGA 41 in the control section 21 at a time of switching from the normal light observation mode NM to the special light observation mode SM, according to the embodiment of the present invention.

FIG. 6 is a flowchart showing an example of a flow of processing of the diaphragm control program executed by the CPU 41a of the FPGA 41 in the control section 21 at the time of switching from the normal light observation mode NM to the special light observation mode SM. In FIG. 6, the same processing steps as those in FIG. 4 are attached with the same step numbers and descriptions thereof will be omitted.

When the endoscope apparatus is operated in the normal light observation mode NM, the CPU 41a determines whether or not an instruction for changing the observation mode to the special light observation mode SM is given (S21). The determination also can be performed depending on whether or not the user gives an instruction for switching to the special light observation mode SM through the mode switching switch 22a.

If an instruction for changing the observation mode to the special light observation mode SM is not given, no processing is performed. When the instruction for changing to the special light observation mode SM is given (S21: YES), the CPU 41a obtains the current diaphragm value DC from the diaphragm driving section 45 on the basis of the feedback signal FB of the diaphragm driving section 45 (S2), and calculates the correction value DA by multiplying the current diaphragm value DC by a predetermined coefficient β (S22). The predetermined coefficient β is a value less than 1, and the value is ½, for example.

Also the predetermined coefficient β may be described in the diaphragm control program or may be set in the storage section 41b. In addition, also the predetermined coefficient β can be changed according to the type or the like of the endoscope 2, light source apparatus 3 or video processor 4.

After that, the CPU 41a executes the processing steps from the step S4 to step S11.

That is, during a period after the instruction for switching from the illumination mode corresponding to the normal light observation mode NM to the illumination mode corresponding to the special light observation mode SM is given through the mode switching switch 22a until the switching performed by the CPU 41a which is the illumination mode switching control section is completed, the diaphragm control section 41c as the illumination light amount control section causes the diaphragm 25 and the diaphragm driving section 45 to execute adjustment of the emission amount of the illumination light on the basis of the correction value DA obtained by correcting the current diaphragm value DC, which is the light amount control signal at the time when the switching is instructed, using the predetermined coefficient β.

FIG. 7 illustrates a change in the diaphragm at the time of switching from the normal light observation mode NM to the special light observation mode SM. FIG. 7 is a view corresponding to FIG. 5.

FIG. 7 illustrates that, when the instruction for switching from the normal light observation mode NM to the special light observation mode SM is given at the time t1, after the time t1, the diaphragm 25 is controlled on the basis of the correction value DA which is a value smaller than the current diaphragm value DC. Therefore, the diaphragm driving control signal IC has a constant value from the time t1 to t2, and the diaphragm 25 is maintained at a constant value.

Furthermore, in the step S9, the CPU 41a controls the input to the control calculation section 51 such that, instead of the target brightness value CSV from the light-adjusting section 32, the reference value RS indicating that the diaphragm 25 is appropriately controlled is inputted to the calculation control section 51.

After the time t1, until the rotary filter 24 is rotated to allow the filter for special light to be appropriately arranged on the optical path of the emitted light from the lamp 23, the light amount of the illumination light with which the subject is irradiated changes. As a result, the luminance of the endoscopic image obtained by the video processing section 34 changes, and the light-adjusting section 32 of the video processor 4 which is in the normal light observation mode NM calculates a target brightness signal CS corresponding to the change to output the calculated target brightness signal CS. However, since the diaphragm 25 is fixed to a value corresponding to the correction value DA, the target brightness value CSV calculated in the light-adjusting section 32 becomes a value greatly different from the reference value RS after the time t1, as shown in FIG. 7.

After that, at the time t2, when the switching from the normal light observation mode NM to the special light observation mode SM is completed and the endoscope apparatus 1 is brought into the special light observation mode SM, the CPU 41a outputs the reference value RS to the diaphragm control section 41c, and thereafter outputs the target brightness signal CS from the light-adjusting section 32 to the diaphragm control section 41c.

As described above, in the normal light observation mode NM, the filter for the normal light observation mode NM is selected in the rotary filter 24. The normal light is light having broader band than that of the special light and larger light amount than that of the special light. Therefore, the luminance of the image pickup signal obtained in the CCD 13 is higher than that in the special light observation mode SM. As a result, the diaphragm 25 is more stopped down in the normal light observation mode NM than in the special light observation mode SM. According to the light source apparatus 3 in the above-described embodiment, the diaphragm driving control signal IC corresponding to the correction value DA which is smaller than the current diaphragm value DC is outputted until the mode switching is completed such that the diaphragm value of the diaphragm 25 becomes close to the diaphragm value in the special light observation mode SM when the observation mode is switched from the normal light observation mode NM to the special light observation mode SM and the control of diaphragm 25 is started in the special light observation mode SM.

Then, after the completion of the mode switching, the diaphragm control section 41 is controlled such that the reference value RS is inputted to the control calculation section 41c of the diaphragm control section 41 and thereafter the target brightness value CSV of the target brightness signal CS from the light-adjusting section 32 is inputted to the control calculation section.

Such control can prevent the entire endoscopic image displayed on the monitor 5 from getting dark for a moment. Furthermore, since the correction value DA is determined using the current diaphragm value DC at the time of the mode switching, even when the lamp 23 is deteriorated, the entire endoscopic image can be prevented from getting dark for a moment.

As described above, the above-described embodiment is capable of providing the light source apparatus and the light-adjusting method for the light source apparatus, which enable halation and the like in an endoscopic image to be prevented at the time of switching of the illumination modes.

As described above, the above-described embodiment is capable of providing the light source apparatus and the light-adjusting method for the light source apparatus, which enable halation and the like in an endoscopic image to be prevented at the time of switching of the modes.

The present invention is not limited to the above-described embodiment but various changes, modifications, or the like are possible without changing the gist of the present invention.

What is claimed is:

1. A light source apparatus comprising:
a light source for supplying illumination light to a subject;
an illumination light amount adjusting section capable of adjusting an emission amount of the illumination light;
an illumination light amount control section that causes the illumination light amount adjusting section to execute adjustment of the emission amount of the illumination light on the basis of a light amount control signal generated based on brightness of an image obtained by picking up an image of the subject;
an illumination mode switching control section that switches between a first illumination mode in which first light is emitted as the illumination light and a second illumination mode in which second light is emitted as the illumination light, the second light having a wavelength band, at least a part of the wavelength band being different from a wavelength band of the first light; and a switching instruction section that gives an instruction for switching between the first illumination mode and the second illumination mode, wherein, during a period after an instruction for switching from one of the first illumination mode and the second illumination mode to the other of the first and second illumination modes is given by the switching instruction section until the switching by the illumination mode switching control section is completed, the illumination light amount control section maintains the light amount control signal at a predetermined value corresponding to the illumination mode after the completion of the mode switching, and causes the illumination light amount adjusting section to execute adjustment of the emission amount of the illumination light on the basis of the maintained value.

2. The light source apparatus according to claim 1, wherein the illumination light amount control section maintains, as the predetermined value, a value of a correction signal obtained by correcting the light amount control signal at a time when the instruction for the switching is given, using a predetermined coefficient corresponding to the illumination mode after the completion of the mode switching, and causes the illumination light amount adjusting section to execute adjustment of emission amount of the illumination light on the basis of the maintained value.

3. The light source apparatus according to claim 1, wherein
the illumination light amount control section includes a control calculation section that receives the light amount control signal, to calculate an adjustment value of the emission amount of the illumination light and output the calculated adjustment value, and
when the switching is completed, the illumination mode switching control section inputs a predetermined signal to the control calculation section and thereafter inputs the light amount control signal to the control calculation section.

4. The light source apparatus according to claim 1, wherein, when a value of the correction signal exceeds a predetermined upper limit value or falls below a predetermined lower limit value, the illumination mode switching control section changes the value of the correction signal to the predetermined upper limit value or the predetermined lower limit value.

5. The light source apparatus according to claim 1, wherein
the light source includes a lamp that emits light, and an optical filter provided so as to be insertable into and removable from an optical path of the light emitted from the lamp, the optical filter being configured to transmit light having a wavelength band which is a part of wavelength band of the emitted light in a state where the optical filter is inserted into the optical path,
the first illumination mode is a mode in which the optical filter is inserted into the optical path and the light transmitted by the optical filter is used as the illumination light,
the illumination light amount adjusting section includes a diaphragm device that adjusts a light amount of the illumination light, and a diaphragm driving section that drives the diaphragm device according to a diaphragm driving control signal inputted thereto, and
the illumination light amount control section generates the diaphragm driving control signal on the basis of the light amount control signal.

6. The light source apparatus according to claim 1, wherein the first illumination mode and the second illumination mode are illumination modes corresponding to observation modes in an endoscope apparatus.

7. The light source apparatus according to claim 6, wherein the first illumination mode and the second illumination mode are a special light observation mode and a normal light observation mode in the endoscope apparatus, respectively.

8. A method for operating a light source apparatus including an illumination light amount adjusting section capable of emitting first light and second light as illumination light to a subject, the second light having a wavelength band, at least a part of the wavelength band being different from a wavelength band of the first light, the illumination light amount adjusting section adjusting an emission amount of the illumination light on the basis of a light amount control signal generated based on brightness of the subject, the method comprising:

switching, by an illumination mode switching control section, from one of a first illumination mode in which the first light is emitted as the illumination light and a second illumination mode in which the second light is emitted as the illumination light to the other of the first and second illumination modes, on the basis of a switching instruction by a switching instruction section that gives an instruction for switching between the first illumination mode and the second illumination mode; and during a period after an instruction for switching from one of the first illumination mode and the second illumination mode to the other of the first and second illumination modes is given by the switching instruction section until the switching of the illumination modes by the illumination mode switching control section is completed, maintaining by the illumination light amount control section the light amount control signal at a predetermined value corresponding to the illumination mode after the completion of the mode switching, and causing the illumination light amount adjusting section to execute adjustment of the emission amount of the illumination light on the basis of the maintained value.

9. The method for operating the light source apparatus according to claim 8, wherein the illumination light amount control section maintains, as the predetermined value, a value of a correction signal obtained by correcting the light amount control signal at a time when the instruction for the switching is given, using a predetermined coefficient corresponding to the illumination mode after the completion of the mode switching and causes the illumination light amount adjusting section to execute adjustment of emission amount of the illumination light on the basis of the maintained value.

10. The method for operating the light source apparatus according to claim 8, wherein, when the switching is completed, a predetermined signal is inputted to the control calculation section which receives the light amount control signal, calculates an adjustment value of the emission amount of the illumination light, and outputs the calculated adjustment value, and thereafter the light amount control signal is inputted to the control calculation section.

11. The method for operating the light source apparatus according to claim 8, wherein when a value of the correction signal exceeds a predetermined upper limit value or falls below a predetermined lower limit value, the value of the correction signal is changed to the predetermined upper limit value or the predetermined lower limit value.

12. The method of operating the light source apparatus according to claim 8, wherein
the light source apparatus includes a lamp that emits light, and an optical filter provided so as to be insertable into and removable from an optical path of the light emitted from the lamp, the optical filter being configured to transmit light having a wavelength band which is a part of wavelength band of the emitted light in a state where the optical filter is inserted into the optical path, the first illumination mode is a mode in which the optical filter is inserted into the optical path and the light transmitted by the optical filter is used as the illumination light, the illumination light amount adjusting section includes a diaphragm device that adjusts a light amount of the illumination light, and a diaphragm driving section that drives the diaphragm device according to a diaphragm driving control signal inputted thereto, and the diaphragm driving control signal is generated on the basis of the light amount control signal.

13. The method of operating the light source apparatus according to claim 8, wherein the first illumination mode and the second illumination mode are illumination modes corresponding to observation modes in an endoscope apparatus.

14. The method for operating the light source apparatus according to claim 13, wherein the first illumination mode and the second illumination mode are a special light observation mode and a normal light observation mode in the endoscope apparatus, respectively.

* * * * *